(12) United States Patent
Luppi et al.

(10) Patent No.: US 9,274,111 B2
(45) Date of Patent: Mar. 1, 2016

(54) METHOD FOR THE DIAGNOSIS OF AND/OR MONITORING MUCORMYCOSIS

(75) Inventors: Mario Luppi, Nonantola (IT); Patrizia Barozzi, Modena (IT); Leonardo Potenza, Modena (IT); Daniela Vallerini, Carpi (IT); Forghieri Fabio, Formigine (IT)

(73) Assignee: Universita' Degli Studi Di Modena E Reggio Emilia, Modena (IT)

( * ) Notice: Subject to any disclaimer, the term of this patent is extended or adjusted under 35 U.S.C. 154(b) by 10 days.

(21) Appl. No.: 13/990,784

(22) PCT Filed: Nov. 24, 2011

(86) PCT No.: PCT/IB2011/055270
§ 371 (c)(1),
(2), (4) Date: May 30, 2013

(87) PCT Pub. No.: WO2012/073160
PCT Pub. Date: Jun. 7, 2012

(65) Prior Publication Data
US 2013/0260395 A1 Oct. 3, 2013

(30) Foreign Application Priority Data
Dec. 1, 2010 (IT) .............................. MI2010A2224

(51) Int. Cl.
*G01N 33/569* (2006.01)

(52) U.S. Cl.
CPC .... *G01N 33/56961* (2013.01); *G01N 33/56972* (2013.01); *G01N 2333/37* (2013.01); *G01N 2333/5406* (2013.01); *G01N 2333/5428* (2013.01); *G01N 2333/57* (2013.01)

(58) Field of Classification Search
None
See application file for complete search history.

(56) References Cited

FOREIGN PATENT DOCUMENTS

| EP | 0957359 A2 | 11/1999 |
|---|---|---|
| WO | 9823960 A1 | 6/1998 |
| WO | 0026248 A2 | 5/2000 |
| WO | 03018051 | 3/2003 |
| WO | 2004005925 A2 | 1/2004 |
| WO | 2008075395 A2 | 6/2008 |
| WO | 2010107500 A1 | 9/2010 |

OTHER PUBLICATIONS

"PCT International Search Report dated Jan. 5, 2012 for PCT/IB2011/055270, from which the instant application is based," 3 pgs.
"Italian Search Report and Written Opinion, with English translation, dated Jun. 29, 2011 for related IT Application No. MI2010A2224," 9 pgs.
Potenza L et al., "Diagnosis of invasive aspergillosis by tracking Aspergillus-specific T cells in hematologic patients with pulmonary infiltrates," Leukemia: Official Journal of the Leukemia Society of America, Leukemia Research Fund, U.K Mar. 2007 vol. 21, No. 3.
Forghieri, F., "Organising pneumonia mimicking invasive funcal disease in patients with lueukaemia," European Journal of Haematology, vol. 85, No. 1, Jul. 1, 2010, pp. 76-82.
Potenza L. et al., Mucorales-specific T cells emerge in the course of invasive mucormycosis and may be used as a surrogate diagnostic marker in high-risk patients, Blood, vol. 118, No. 20, Sep. 19, 2011, pp. 5416-5419.
Romani, L., "Immunity to Fungal Infections," Nature Reviews, vol. 4, 2004, 1-13.
Lass-Florl, C., "Zygomycosis: conventional laboratory diagosis," Journal Compilation 2009 European Society of Clinical Microbiology and Infectious Diseases, 2009, CMI, 15 (Suppl. 5), 60-65.
Torres-Narbona, M. et al., "Impact of Zygomycosis on Microbiology Workload: a Survey Study in Spain," Journal of Clinical Microbioloty, Jun. 2007, vol. 45, No. 6, 2051-2053.
Chayakulkeeree, M., et al., "Zygomycosis: the re-emerging fungal infection," Eur J Clin Microbiol Infect Dis (2006) 25: 215-229.
Goodyear, O.C. et al., "Differential pattern of CD4+ and CD8+ T-cell immunity to MAGE-A1/A2/A3 in patients with monoclonal gammopathy of undetermined significance (MGUS) and multiple myeloma," Blood, Oct. 15, 2008, vol. 112, No. 8, 3362-3372.
Chamilos, G. et al., "Delaying Amphotericin B-Based Frontline Therapy Significantly Increases Mortality among Patients with Hematologic Malignancy Who Have Zygomycosis," Clin. Infect. Dis. 47: Aug. 15, 2008, 503-509.
Cenci, E. et al., "Th1 and Th2 Cytokines in Mice with Invasive Aspergillosis," Infection and Immunity, Feb. 1997, vol. 65, No. 2, 564-570.
Lalvani, A., "Diagnosing Tuberculosis Infection in the 21st Century: New Tools to Tackle an Old Enemy," Chest., 131: 2007, 1898-1906.
Comoli, P. et al., "Infusion of autologous Epstein-Barr virus (EBV)-specific cytotoxic T cells for prevention of EBV-related lymphoproliferative disorder in solid organ transplant recipients with evidence of active virus replication," Blood, Apr. 1, 2002 vol. 99, No. 7, 2592-2598.
Hata, D.J. et al., "Real-Time PCR Method for Detection of Zygomycetes," Journal of Clinical Microbiology, Jul. 2008, vol. 46, No. 7, 2353-2358.
Hebart, H. et al., "Analysis of T-cell responses to Aspergillus fumigatus antigens in healthy individuals and patients with hematologic malignancies," Blood, Dec. 15, 2002, vol. 100, No. 13, 4521-4528.
Bialek, R. et al., "PCT based indentification and discrimination of agents of mucormycosis and aspergillosis in paraffin wax embedded tissue," J Clin Pathol 2005 58: 1180-1184.

(Continued)

*Primary Examiner* — S. Devi
(74) *Attorney, Agent, or Firm* — Fredrikson & Byron, P.A.

(57) ABSTRACT

A method is described for the diagnosis and/or monitoring of active or previous infection by *Mucor* which consists in the identification of Mucorales-specific T cells in samples from biological fluids taken from the patient and put into contact with a *Mucor* antigen. These specific immune responses can be detected by the execution of immunoenzymatic assays (ELISPOT, Quantiferon) or of immunocytofluorimetric assays [Cytokine Secretion Assay (CSA), Intracellular Cytokine Staining (ICS)] in vitro. In greater detail, the method in question provides for checking for the presence of specific IFN-γ producing T cells, of specific IL-10 producing T cells and/or specific IL-4 producing T cells.

11 Claims, 2 Drawing Sheets

(56) References Cited

OTHER PUBLICATIONS

Jaimes, M.G. et al., "Quality assurance of intracellular cytokine staining assays; Analysis of multiple rounds of proficiency testing," Journal of Immunological Methods, 11132; (2010) 1-15.

Kasai, M. et al., "Detection of a Molecular Biomarker for Zygomycetes by Quantitative PCR Assays of Plasma, Bronchoalveolar Lavage, and Lung Tissue in a Rabbit Model of Experimental Pulmonary Zygomycosis," Journal of Clinical Microbigology, No. 2008, vol. 46, No. 11, 3690-3702.

Lalvani, A., "CD8 Cytotoxic T Cells and the Development of New Tuberculosis Vaccines," Am. J. Respir. Crit. Care Med., vol. 166, (2002), 789-790.

Roden, M.M. et al., "Epidemology and Outcome of Zygomycosis: A Review of 929 Reported Cases," Clin. Infec. Dis. 41: (2005) 634-653.

Potenza, et al. 'Mucorales-specific T cells emerge in the course of invasive mucormycosis and may be used as a surrogate diagnostic marker in high-risk patients', Sep. 19, 2011, Figure 1, Published in Blood Online. [online—serial]: The American Society of Hematology, [retrieved on Sep. 14, 2015]. Retrieved from www.bloodjournal.com. DOI: 10.1182/blood-2011-07-366526. ISSN 1528-0020.

Potenza, et al. 'Mucorales-specific T cells emerge in the course of invasive mucormycosis and may be used as a surrogate diagnostic marker in high-risk patients', Nov. 17, 2011, vol. 118, No. 1734, pp. 5416-5419. Published in Blood Online. [online—serial]: The American Society of Hematology, [retrieved on Sep. 14, 2015]. Retrieved from www.bloodjournal.com. DOI: 10.1182/blood-2011-07-366526.

Kwon-Chung, Kyung J. 'Taxonomy of Fungi Causing Murcormycosis and Entomophthoramycosis (Zygomycosis) and Nomenclature of the Disease: Molecular Mycologic Perspectives', 2012, pp. S8-S15. Published by Oxford University Press [online]: Infectious Diseases Society of America, [retrieved on Sep. 11, 2015]. Retrieved from http://cid.oxfordjournals.org/. DOI: 10.1093/cid/cir864.

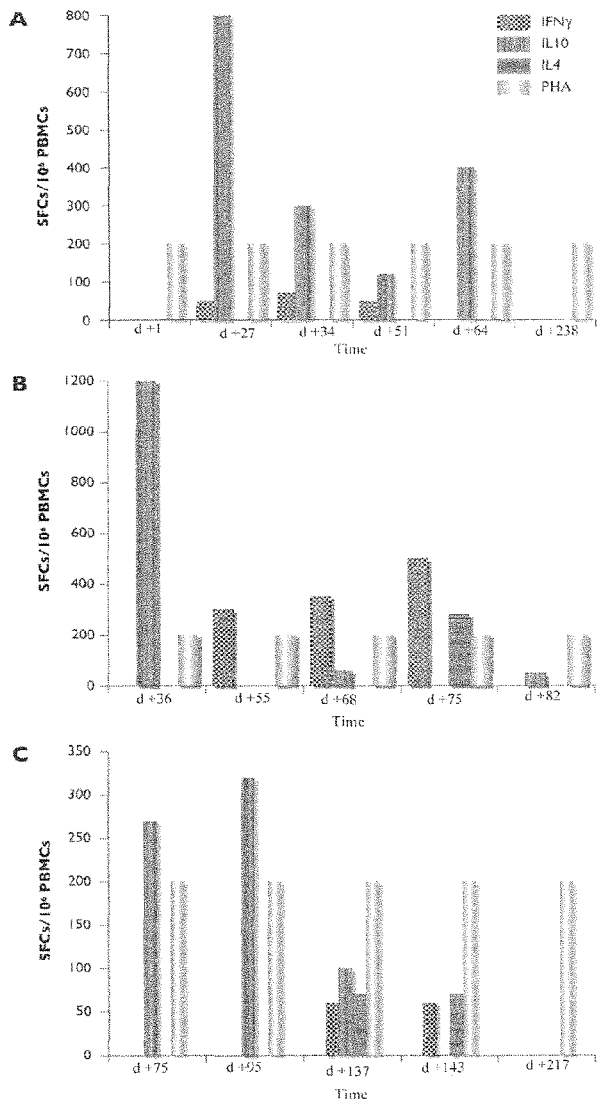

Figure 1

Legend. Mucorales-specific T cells in the three patients with Invasive Mucormycosis. Columns with black squares = IFN-γ producing Mucorales-specific T cells; columns with vertical black stripes = IL-10 producing Mucorales-specific T cells; columns with horizontal black stripes = IL-4 producing Mucorales specific T cells; white columns = response of the T cells to the mitogen phytohaeoagglutinin (PHA).

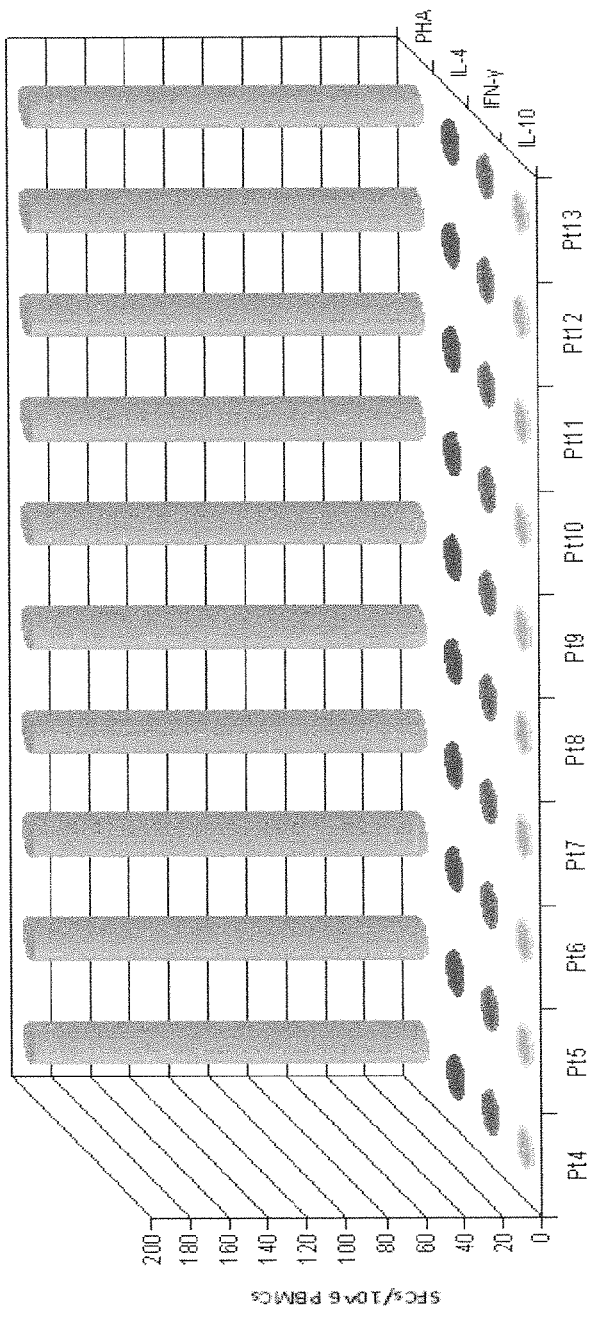

Figure 2

Results of the ELISpot test in the 10 patients with infections of known aetiology but other than Invasive Mucormycosis Columns with vertical black stripes = IL-10 producing Mucorales-specific T cells; columns with black squares = IFN-γ producing Mucorales-specific T cells; black columns = IL-4 producing Mucorales-specific T cells; grey columns = response of the T cells to the mitogen phytohaemoagglutinin (PHA).

METHOD FOR THE DIAGNOSIS OF AND/OR MONITORING MUCORMYCOSIS

RELATED APPLICATIONS

This application is a 35 U.S.C. 371 national stage filing from International Application No. PCT/IB2011/055270 filed Nov. 24, 2011, which claims priority to Italian Application No. MI2010A002224 filed Dec. 1, 2010, the teachings of which are incorporated herein by reference.

The present invention relates to a method for the diagnosis and/or monitoring of active or previous infection by *Mucor* which consists in the identification of Mucorales-specific T cells in samples of biological fluids which have been taken from the patient and put in contact with a *Mucor* antigen. These specific immune responses can be detected by performing immunoenzymatic assays (ELISPOT, Quantiferon) (Lalvani, Chest., 131: 1898-1906, 2007) or immunocytofluorimetric assays [Cytokine Secretion Assay (CSA) (Goodyear et al., Blood, 112: 3362-3372, 2008)], Intracellular Cytokine Staining (ICS) (Jaimes et al., J. Immunol. Method, 1-15, 2010)] in vitro, which are incorporated herein by reference. In greater detail, the method in question provides for checking for the presence of specific IFN-γ producing T cells, of specific IL-10 producing T cells, and/or of specific IL-4 producing T cells.

STATE OF THE ART

Invasive fungal infections (IFIs) represent an important cause of morbidity and mortality in patients suffering from malignant haemopathy who undergo not only allogeneic bone marrow transplantation but also standard chemotherapy. The risk of death in patients suffering from IFIs reaches percentages as high as 90%.

The aetiological agent that is mostly responsible for IFIs is represented by fungi of the species *Aspergillus* which accounts for slightly more than 50% of all invasive fungal infections. However, in recent years, fungi of the order Mucorales [Note by the inventors: A recent reclassification abolished the order Zygomycetes and included fungi of the order Mucorales in the provisional subphylum Mucoromycotina, and fungi of the order Entomophthorales in that of Entomophthoromycotina; pending a definitive reclassification and a reintroduction of the order Zygomycetes, since the Entomophthorales cause low level and chronic infections that are almost never invasive and never in patients with malignant haemopathies, in this text, invasive infections by Mucorales will be treated as synonymous with the infections previously known as Invasive Zygomycosis] have become the second most common agent responsible for invasive fungal infections with percentages variable from 3% to 15%, according to case histories. Invasive Mucorales (IM) infections have very high mortality percentages of from 70% to 90% of patients affected. The causes of such high mortality lie in the lack of diagnostic methods that permit certain and timely diagnosis of mucormycosis. It has been estimated that, in the case of IM, a delay of six days in starting an effective antifungal treatment after the appearance of the first symptoms of IM is associated with a doubling in mortality and a reduction in survival to 12 weeks for all but 20% of patients (Chamilos et al., Clin. Infect. Dis.; 47: 503-509, 2008).

The diagnostic methods that are currently in use for the diagnosis of IM are represented almost exclusively by histological examination and cultural examination. However, both are greatly limited by: a) invasiveness and difficulty in obtaining a biopsy sample because of the clinical conditions of the patients affected; b) low sensitivity (cultural examination is positive in a percentage of about 10-20% of cases (Lass-Florl. Clin. Microbiol. Infect.; 15: 60-65, 2009), c) contamination of the sample by environmental fungi (in one study only 7.6% of cultural samples on which Mucorales were detected came from patients actually affected by IM) (Torres-Narbona et al., J. Clin. Microbiol; 2051-2053, 2007); d) factors adversely affecting the growth of these fungi in culture, such as cold and protein inhibitors; e) difficulty in isolating Mucorales from cultural examinations of peripheral blood (Chayakuleeree M, Eur. J. Microbiol. Infect. Dis.; 25: 215-229, 2006).

Moreover, the radiological signs which are encountered most frequently in IM cases upon computerized axial tomography (CT), are not able to differentiate IM from Invasive Aspergillosis since both pathogens are angioinvasive and often present the same radiological characteristics (Roden et al., Clin. Infect. Dis. 41: 634-653, 2005). Finally, the polymerase chain reaction (PCR) for the amplification and the examination of Mucorales nucleic acids on biological materials lacks standardization and is used almost exclusively as a confirmation test on biopsy material and not as a screening test on plasma and hence has the same limitations of access as biopsy examination (Bialek et al., J. Clin. Pathol., 58: 1180-1184, 2005; Kasai et al, J. Clin. Micriobiol., Vol. 46, No. 11, 3690-3702, 2008; Hata et al., J. Clin, Microbiol., Vol. 46, No. 7, 2353-2358, 2008).

The diagnosis of IM is thus based on greater or lesser degrees of probability and is very rarely made with certainty, and often belatedly in relation to the course of the infection. Recent studies, firstly in mice and subsequently also in man, have shown that adaptive immunity, that is, that represented by the T cells, plays a predominant role in the host's defences against fungi. In particular, a cell-mediated immunity polarized to type 1 helper T cells (Th1) producing interferon gamma (IFN-γ) is protective with respect to fungal infections, particularly Invasive Aspergillosis whereas a cell-mediated immunity polarized to type 2 helper T cells (Th2) producing interleukin 10 (IL-10) is permissive with respect to IA (Cenci et al. Infection and Immunity, Vol. 65. No. 2, 564-570, 1997; Hebart et al., Blood, Vol. 100, No. 13, 4521-4528, 2002; Romani, Nature Reviews, Vol, 4, 1-13, 2004). The ELISPOT method (Enzyme-linked ImmunoSpot Assay) has been shown to be a sensitive and specific tool in the diagnosis of infection by tuberculosis mycobacteria or in infections of viral origin, both in immunocompetent patients and in immunosuppressed patients, by means of a search for T cells that are specific to the mycobacterium (Lalvani, Am. J. Respir. Crit. Care Med., Vol. 166, 789-790, 2002) or by the isolation of T cells that are specific to the Epstein-Barr virus in patients undergoing kidney transplant (Comoli et al., Blood, 99: 2592-2598, 2002).

ELISPOT is an assay based on the cell immunological response to a specific antigen. This method is generally implemented on plates with 96 wells, coated with specific monoclonal antibodies, in which the cells and the specific antigen are incubated for 6-48 hours.

During this period, the cell response takes place and the specific cytokines are produced, according to the type of antibody/antigen used, and give rise to spots that are detected and counted by conventional image-analysis software.

The ELISPOT method for a generic evaluation of blood cell activity is described in European patent application EP0957359 (Volkmar et al.), which is incorporated herein by reference.

The ELISPOT method applied to T lymphocytes for the diagnosis or monitoring of diseases such as hepatitis B, hepatitis C, tuberculosis, malaria, HIV or influenza is described in International patent application WO98/23960 (Lalvani et al.), which is incorporated herein by reference.

The ELISPOT method applied to T lymphocytes that are reactive to antigens derived from the protein ESAT-6, which is expressed by Mycobacterium tuberculosis, for the diagnosis of tuberculosis, or even purely contact of the host with the pathogen (latent disease) is described in International patent application WO00/26248 (Lalvani et al.), which is incorporated herein by reference.

A further ELISPOT method applied to T lymphocytes that are reactive not only to antigens derived from ESAT-6 but also from the protein CFP-10 is described in International patent application WO2004/005925 (Lalvani et al.), which is incorporated herein by reference.

The ELISPOT method applied to T lymphocytes which are reactive to antigens of hyphae and conidia of *Aspergillus fumigatus* for the diagnosis of Invasive Aspergillosis is described in International patent application WO2008/075395 (University of Modena and Reggio Emilia), which is incorporated herein by reference.

Up to now, the ELISPOT method has thus been used for diseases of viral origin and for bacterial infections, in particular for infections by Mycobacterium tuberculosis whereas, for fungal infections, it has been used solely for the invasive form of infections by *Aspergillus fumigatus*.

BRIEF DESCRIPTION OF THE DRAWINGS

FIGS. 1A to 1C show Mucorales-specific T cells in the three patients with Invasive Mucormycosis.

FIG. 2 shows the results of ELISPOTs in patients affected by pulmonitis with non-fungal aetiology, used as negative controls.

DESCRIPTION OF THE INVENTION

It is known that immunoenzymatic assays, in particular ELISPOT assays, and immunocytofluorimetric assays can advantageously be used for diagnosis, in particular early diagnosis and/or monitoring also of fungal infections, particularly in the case of Invasive Mucormycosis (IM).

The objective of the invention is to utilize these assays and, in particular, the ELISPOT assay, for the identification and counting of T cells specific to Mucorales, so that simply the detection of IFN-γ producing cells, of IL-10 producing cells and/or of IL-4 producing cells can be used for the determination of the risk of infection, for the diagnosis of IM, for the monitoring of active or previous infection, and for improving the clinical management of patients who are at risk of and/or suffering from this pathology.

The subject of the present invention is therefore a method for the diagnosis and/or monitoring of IM which comprises the execution of an immunoenzymatic or immunocytofluorimetric assay in vitro on microtitration plates such as, for example, the type with 96 wells, characterized in that the biological fluid taken from the patient is put into contact with an antigen of fungi of the Mucorales class, in particular an extractable Mucorales antigen.

According to one aspect of the present invention, the method permits the identification and counting of T cells that are specific to Mucorales in order to check for the presence of and/or to define a ratio between those producing IFN-γ, those producing IL-10, and/or those producing IL-4.

According to the present invention, the immunoenzymatic assay is ELISPOT assay (Enzyme-Linked ImmunoSpot Assay) and the antigen, which is preferably an extractable antigen, can be obtained from conidia of Mucorales or from hyphae of Mucorales.

Conidia (or conidiospores) are the predominantly unicellular reproductive structures of the fungus which are formed at the tips of the hyphae which in turn are cylindrical unicellular or multicellular filaments; when arranged on top of one another, these form the mycelium or the vegetative bodies of the fungi.

In particular, according to an embodiment of the present invention, the antigen is obtained from conidia of Mucorales which are collected after culture for two-four days, preferably for three days, preferably on Saboraud agar medium, filtered through sterile gauze. After filtration, the conidia are placed in liquid Saboraud medium and stirred for about 6-18 hours, preferably 12 hours, to achieve germination which enables the antigenic determinants to be displayed. The germinated conidia are washed in saline solution (PBS), deactivated by heat, preferably for about 1 hour at 100° C., and counted. The antigens are then treated by sonication, preferably with the use of an ultrasound homogenizer reaching a maximum power of 400 W and working at a frequency of 24 Khz. The conidia are subjected to 4 sonication cycles of about 10 seconds duration, each at about 70% of maximum power. Finally, the germinated and sonicated conidia are stored in PBS or culture medium at between about −30 and −10° c., preferably at −20° C.

According to another embodiment of the present invention, the antigen, which is preferably an extractable antigen, is obtained from hyphae of Mucorales which are homogenized, for example, with the use of a mortar with beads made of an inert material, preferably glass beads in buffer, preferably 50 mM Tris-HCl buffer with a pH of about 7.5. The proteinaceous extract thus obtained is recovered after centrifuging at between 10 and 14,000 rpm for about 10 minutes and kept at a temperature of between about −30 and −10° C., preferably −20° C.

For the purposes of the present invention, the expression "Mucorales antigen" thus means a constituent of the fungus structure which is treated in a manner such that it is capable of stimulating a specific T cell response.

The biological fluid that is used according to the method of the present invention may be blood, bronchioalveolar lavage liquid (BAL), or pleural liquid from patients who are at risk of or already infected by Mucormycosis.

In particular, the fluid may be obtained by citrated endovenous sampling, preferably of about 20 ml, by citrated pleural liquid sampling, preferably of about 20 ml, or by citrated BAL liquid sampling, preferably of about 30 ml.

According to the method of the present invention, the mononucleated cells or purely the isolated T lymphocytes from the endovenous blood samples may be used.

According to the present invention, the sample of blood, pleural liquid, or bronchioalveolar lavage liquid is diluted with an approximately equal volume of culture medium, for example RPMI 1640, and is then centrifuged on density gradient (FICOLL, LYMPHOPREP) to separate the population of mononucleated cells (PBMCs). After 2 washings, for example, in RPMI 1640, the cells are frozen, preferably in liquid nitrogen, even more preferably in the presence of 20% DMSO and 50% foetal bovine serum (FBS) for the ELISPOT tests.

The cell samples are then thawed slowly in a bath kept thermostatically at 35-40° C., preferably about 37° C. DNAse is added to a final concentration of about 10 mg/ml and left to act at ambient temperature for about 20 minutes. The cells are transferred into a test tube and resuspended carefully with about 10 ml of RPMI 1640 medium supplemented with about 5% of FBS, which is added dropwise. After a first centrifuging at about 1,000 rpm for about 10', the cell pellet obtained is resuspended in R10 culture medium (RPMI 1640; 10% FBS; 1% sodium pyruvate; 1% ampicillin; 0.5% gentamicin; 18 UI/ml IL-2) and the cells are then counted in a Bürker chamber. A "Pan Cell Isolation Kit, human" distributed by Miltenyi Biotech S.r.l. (Calderara di Reno, Bologna, Italy) has been used for the separation of the CD3+ T cells. The CD3+ T cells are separated by depletion of the non-T cells (negative selection). The non-T cells, marked with a cocktail of biotin-conjugated monoclonal antibodies (CD14, 16, 19, 36, 56, 123 and Glycophorin A) are reacted with conjugated anti-biotin monoclonal antibodies with magnetic micro-beads. The marked cells (non-T cells) and the non-marked (CD3+ T cells) are passed through a MACS-MS column (Miltenyi) in the presence of a magnetic field, allowing the CD3+ T cells to pass through and the non-T cells to be blocked. The separation process is carried out on cell samples after thawing, following the instructions provided by Miltenyi.

According to another embodiment of the present invention, the antigen may be obtained from conidia of Mucorales which are collected after culture for 2-4 days (for example, on Saboraud agar medium) by washing of the surface layer of the fungal culture with sterile water. The washing liquid obtained is filtered through sterile gauze and centrifuged at between 10,000 and 15,000 rpm, preferably at about 12,000 rpm, for 5-15 minutes, preferably 10 minutes. The supernatant liquid is removed and the conidia pellet thus obtained is resuspended in liquid Saboraud and stirred for 6-18 hours, preferably for about 12 hours to achieve germination. The germinated conidia are washed in saline solution (PBS), deactivated by heat, preferably for about 1 hour at 100° C., and counted. The antigen (2-4 million germinated conidia) is then treated by sonication, preferably with the use of an ultrasound homogenizer reaching a maximum power of 400 W and working at a frequency of 24 KHz. The conidia are subjected to 4 sonication cycles, each of about 10 seconds duration, preferably at 70% of maximum power. Finally, the germinated and sonicated conidia are resuspended in PBS or culture medium (1 ml) and are used immediately or stored at about −20° C. and used subsequently. The conidia thus obtained are used in the ELISPOT test at a final concentration of about 100,000-200,000 conidia/ml and in the CSA test at a concentration of 200,000-400,000 conidia/ml.

According to a further embodiment of the present invention, the extractable antigen may be obtained from hyphae of Mucorales which are collected by scraping of several culture plates with a scalpel blade and resuspended in sterile water. After vortexing, filtration is performed through sterile gauze to eliminate any agar. The mycete thus obtained is centrifuged at about 15,000 rpm for about 10 minutes and then, when the supernatant fluid has been removed, is frozen in liquid nitrogen for about 12 hours. The thawed mycete is then homogenized in a mortar in the presence of a volume of beads made of inert material, preferably glass beads, which is equal to the volume of the mycete, in buffer, preferably 50 mM Tris-HCl buffer at a pH of about 7.5. The proteinaceous extract thus obtained is recovered after centrifuging at about 14,000 rpm for about 20'. After evaluation of the protein content, the hyphae extract is used in the ELISPOT test at a final concentration of about 6-10 microgrammes/ml and in the CSA test at a final concentration of 10 microgrammes/ml.

The antigen obtained may be used immediately or may be stored by freezing to about −20° C. and used subsequently.

For the purposes of the present invention, the positivity threshold, that is, the minimum number of specific IFN-γ producing T cells, specific IL-10 producing T cells and/or specific IL-4 producing T cells that is considered indicative of the presence of Invasive Mucormycosis is between 2 and 10 SFCs, preferably 5 SFCs.

EXPERIMENTAL SECTION

ELISPOT Method for Mucorales-Specific IFN-Gamma Producing T Cells 96-well microtitration plates (Multiscreen HTS IP Sterile Plate), distributed by Millipore (Bedford, Mass., USA) and included in the ELISPOT IFN-gamma kit distributed by Mabtech (Nacka Strand, Sweden) were used for all of the ELISPOT tests. The bases of the wells of the plates were made of nitrocellulose and were coated with a specific IFN-γ monoclonal antibody. The plates were removed from the packaging and washed 4 times with PBS 1× (200 μl/well). The plates were fixed with R10 (200 μl/well) and incubated at ambient temperature for ≥30'.

The fixing means were removed and 100,000-200,000 cells in R10 were dispensed into the individual wells (final volume 100-150 μl/well) and then stimulated with sonicated, germinated conidia, deactivated by heat ($1-2\times10^5$ conidia/ml) or with proteinaceous extract (6-10 μg/ml) during incubation at 37° C. in the presence of $CO_2$, (5%) for about 20 hours.

The positive controls were constituted by the same cells incubated with phytohaemagglutinin (PHA) (25 μg/ml) or with a human anti-CD3 antibody (Mabtech) used at a dilution of 1:1,000; the negative control was constituted by the cells alone without any stimulation. All of the tests were carried out in triplicate. After incubation, the plate was emptied and subjected to 5 successive washings with PBS, 200 μl per well. The cytokine-antibody complexes were stained by enzymatic reaction and the addition of a chromogenic substrate: 100 μl of secondary antibody conjugated with alkaline phosphatase, distributed by Mabtech, diluted 1:200 in PBS 1× and 0.5% of foetal bovine serum (FBS) was dispensed into each individual well and, after incubation for 120' at ambient temperature, the substrate, 100 μl (BCIP/NTB-plus), also distributed by Mabtech, was added. The reaction with the substrate was stopped after 12-15' by washing the plate with running water. The nitrocellulose membrane was dried in air for at least 4 hours. Each individual spot which appeared on the base of the well corresponded to the secretion of the cytokine of a single cell (spot forming cell: SFC). The spots were then counted automatically by means of an image-analysis tool (AID ELISPOT Reader System, Amplimedical) controlled by software capable of providing a quick and easy evaluation of the spots on the basis of their size and intensity.

ELISPOT Method for Mucorales-Specific IL-10 Producing T Cells 96-well microtitration plates (Multiscreen HTS IP Sterile Plate), distributed by Millipore (Bedford, Mass., USA) and included in the ELISPOT IL-10 kit distributed by Mabtech (Nacka Strand, Sweden), were used for all of the ELISPOT tests. The bases of the wells of the plate were made of nitrocellulose and were coated with a specific IL-10 monoclonal antibody. The plates were removed from the packaging and washed 4 times with PBS 1× (200 μl/well). The plates were fixed with R10 (200 μl/well) and incubated at ambient temperature for ≥30'.

The fixing means were removed and 30,000-100,000 cells in R10 were dispensed into the individual wells (final volume of 100-150 μl/well) and then stimulated with sonicated, germinated conidia, de-activated by heat ($1-2\times10'$ conidia/ml) or with proteinaceous extract (6-10 μg/ml) during incubation at 37° C. in the presence of $CO_2$, (5%) for about 40 hours. The positive controls were constituted by the same cells incubated with phytohaemagglutinin (PHA) (25 µg/ml) or with a human anti-CD3 antibody (Mabtech) used at a dilution of 1:1,000; the negative control was constituted by the cells alone, without any stimulation. All of the tests were carried out in triplicate. After incubation, the plate was emptied and subjected to 5 successive washings with PBS, 200 µl per well. The cytokine-antibody complexes were stained by enzymatic reaction and the addition of a chromogenic substrate: 100 µl of secondary antibody conjugated with alkaline phosphatase, distributed by Mabtech, diluted 1:200 in PBS 1× and 0.5% foetal bovine serum (FBS), was dispensed into each individual well and, after incubation for 120' at ambient temperature, the substrate 100 µl (BCIP/NTB-plus), also distributed by Mabtech, was added. The reaction with the substrate was stopped after 30-40' by washing the plate with running water. The nitrocellulose membrane was dried in air for at least 4 hours. Each individual spot which appeared on the base of the well corresponded to the secretion of the cytokine of a single cell (spot forming cell: SFC). The spots were then counted automatically by means of an image-analysis tool (AID ELISPOT Reader System, Amplimedical) controlled by software capable of providing a quick and easy evaluation of the spots on the basis of their size and intensity.

ELISPOT Method for Mucorales-Specific IL-4 Producing T Cells 96-well microtitration plates (Multiscreen HTS IP Sterile Plate), distributed by Millipore (Bedford, Mass., USA) and included in the ELISPOT IL-10 kit distributed by Mabtech (Nacka Strand, Sweden) were used for all of the ELISPOT tests. The bases of the wells of the plate were made of nitrocellulose and were coated with a specific IL-4 monoclonal antibody. The plates were removed from the packaging and washed 4 times with PBS 1× (200 µl/well). The plates were fixed with R10 (200 µl/well) and incubated at ambient temperature for ≥30'.

The fixing means were removed and 100,000-250,000 cells in R10 were dispensed into the individual wells (final volume of 100-150 µl/well) and then stimulated with sonicated, germinated conidia, deactivated by heat ($1-2 \times 10^5$ conidia/ml) or with proteinaceous extract (6-10 µg/ml) during incubation at 37° C. in the presence of $CO_2$ (5%) for about 40 hours. The positive controls were constituted by the same cells incubated with phytohaemagglutinin (PHA) (25 µg/ml) or with a human anti-CD3 antibody (Mabtech) used at a dilution of 1:1,000; the negative control was constituted by the cells alone, without any stimulation. All of the tests were carried out in triplicate. After incubation, the plate was emptied and subjected to 5 successive washings with PBS, 200 µl per well. The cytokine-antibody complexes were stained by enzymatic reaction and the addition of a chromogenic substrate: 100 µl of secondary antibody conjugated with alkaline phosphatase, distributed by Mabtech, diluted 1:300 in PBS 1× and 0.5% foetal bovine serum (FBS), was dispensed into each individual well and, after incubation for 120' at ambient temperature, the substrate, 100 µl (BCIP/NTB-plus), also distributed by Mabtech, was added. The reaction with the substrate was stopped after 30-40' by washing the plate with running water. The nitrocellulose membrane was dried in air for at least 4 hours. Each individual spot which appeared on the base of the well corresponded to the secretion of the cytokine of a single cell (spot forming cell: SFC). The spots were then counted automatically by means of an image-analysis tool (AID ELISPOT Reader System, Amplimedical) controlled by software capable of providing a quick and easy evaluation of the spots on the basis of their size and intensity.

Preparation of the Antigen from Mucorales Conidia

After culture of Mucorales for three days on Saboraud agar medium, the conidia were collected by washing of the surface layer of the culture with 30 ml of sterile water. The washing liquid was filtered through sterile gauze and then centrifuged at 12,000 rpm for 10 minutes.

The supernatant liquid was removed and the conidia pellet thus obtained was resuspended in liquid Saboraud and stirred for 12 hours to achieve germination. The germinated conidia were washed in saline solution (PBS), deactivated by heat for 1 hour at 100° C., and counted. The antigen (2-4 million germinated conidia) was then treated by sonication with the use of an ultrasound homogenizer reaching a maximum power of 400 W and working at a frequency of 24 KHz. The conidia were subjected to 4 sonication cycles, each of 10 seconds duration, at 70% of maximum power. Finally, the germinated and sonicated conidia were resuspended in PBS or culture medium (1 ml) and were used immediately or stored at −20° C. and used subsequently.

The conidia thus obtained were used in the Elispot test at a final concentration of about 100,000-200,000 conidia/ml and in the CSA test at a concentration of 200,000-400,000 conidia/ml.

Preparation of the Antigen from Mucorales Hyphae

After culture of Mucorales on Saboraud agar medium, several culture plates were scraped and the scraped product was suspended in 30 ml of sterile water.

The suspension obtained was stirred in a vortex, filtered through sterile gauze and centrifuged at 15,000 rpm for 10 minutes.

The supernatant liquid was then removed and the mycete pellet frozen for 12 hours in liquid nitrogen.

The mycete pellet was then thawed and homogenized in a mortar with an equal volume of fungus/beads in 50 mM Tris-HCl buffer at a pH of about 7.5.

The homogenate obtained was centrifuged at 14,000 for 20 minutes and the proteinaceous content was evaluated.

Finally, the hyphae obtained could be used directly in the ELISPOT test according to the present invention at a concentration of 6-10 µg/ml. Alternatively, the hyphae were frozen to −20° C. until the time of use according to the present invention.

CLINICAL STUDY

In order to evaluate whether the determination and the counting of the Mucorales-specific IFN-γ-Th1, IL-10 (IL-10-Th2) and IL-4 (IL-4-Th2) producing T cells by means of the enzymatic immunospot (ELISPOT) and immunofluorimetric (CSA) assays could improve the clinical diagnosis and monitoring of IZ, clinical tests were carried out on a series of 13 haematological patients with radiologically and clinically documented neutropenia and infections and five healthy donors. Three of the haematological patients with infections were suffering from proven Invasive Zygomycosis.

Mononucleated peripheral blood cells (PBMCs) were separated from each patient or healthy subject by centrifuging on a FICOLL-Hypaque gradient (Linaris, Bettingen am Main, Germany) and then put in culture, some in 96-well polyvinylidene fluoride plates with anti-IFN-gamma, anti-IL-10 and anti-IL-4 monoclonal antibodies (Mabtech, Nacka Strand, Sweden), and some stimulated with the antigens described below in order then to be analyzed with a cytofluorimeter. The cells were stimulated with germinated conidia, deactivated by heat and sonicated, prepared from Mucorales isolated from the patient, and/or with a water-soluble cell extract of Mucorales with PHA and with anti-CD3 $1 \times 10^5$ cells/well were put in culture for sixteen hours in IFN-gamma assay whereas $3 \times 10^4$ cells/well and $2 \times 10^5$ cells/well were put in culture for 40 hours in IL-10 and IL-4 assay, respectively.

All of the test conditions were implemented in triplicate and the results were considered positive if: 1) the number of spot forming cells (SFC)/$10^6$ cells in Mucorales-antigen-stimulated wells was twice as great as in the control wells (cells in non-Mucorales-antigen-stimulated wells) and there were at least 20 spots, and/or 2) the difference in SFC between negative and stimulated was greater than or equal to 5.

The first patient was a 54-year-old man who, on day 16 of the chemotherapy induction cycle for acute myeloid leukaemia (AML), during the neutropenic phase, had developed fever and a right pulmonary lesion. An empirical antibiotic treatment with glycopeptides and carbapenemes and treatment with L-amB at a dosage of 3 mg/kg/die were undertaken. Culture and molecular examinations of blood, urine, faeces and bronchioalveolar lavage liquid (BALf) were repeatedly negative for the presence of bacteria, fungi or viruses. On day 22, a volumetric enlargement of the right pulmonary lesion was found. On day 36, a further enlargement of the nodular consolidation area was observed. On day 47, a surgical resection of the pulmonary lesion was performed. On day 52, the histological report of the pulmonary biopsy was compatible with Invasive Mucormycosis. On day 58, cultural examination on the pulmonary biopsy and molecular examination characterized a mycete of the species *Rizhopus pusillus*. The patient achieved complete remission of the haemopathy and undertook secondary anti-mycotic prophylaxis with posaconazole and then underwent a consolidation chemotherapy cycle.

The second patient was a 68-year-old woman suffering from severe aplastic anaemia (SAA) who, on day 26 of immunosuppressive treatment, had fever and a voluminous paratracheal lymphonodal conglomeration upon high-resolution computerized tomography (HRCT) of the thorax. Cultural and molecular examinations of blood, urine, and faeces were repeatedly negative for the presence of bacteria, fungi or viruses. On day 28 of the immunosuppressive treatment, bronchoscopy showed infiltration of the trachea with complete destruction of the cartilaginous structure. Multiple biopsies were performed. On day 33, histological examination of the tracheal biopsy showed fungal hyphae compatible with infection by filamentous fungus, most probably *Aspergillus*. Treatment with L-amB was undertaken at a dosage of 5 mg/kg/die. On day 35, cultural examination on BAL liquid was positive for *Mucor* spp. On day 36 A Y-shaped tracheal stent was put in place. On day 41, cultural examination performed on the tracheal biopsy was also positive for *Mucor* spp. A control HRCT of the thorax showed the tracheal compression unchanged. On day 49, an oesophageal ulcer by ab-extrinsec infiltration was found. On day 55, a tracheo-oesophageal fistula was found. On day 64, posaconazole was combined with the L-amB. On day 77, occlusion of the left branch of the tracheal stent by granulomatous reaction was recorded. On day 84, a new bronchoscopy was performed and it was impossible to remove the stent and open the left bronchus. The patient's dyspnoea worsened progressively until it led to the patient's death on day 88 from the start of immunosuppressive therapy.

The third patient was a 36-year-old man suffering from acute promyelocytic leukaemia (APL) who, on day 35 of induction treatment with anthracycline and all-transretinoic acid (ATRA) had developed diplopia and cephalea. An encephalo-CT was negative. Morphological and cultural examinations on cephalorachidian fluid were negative for the presence of bacteria, fungi or viruses or for localization of APL. On day 42, owing to the appearance of sx palpebral ptoses, an encephalo-NMR was performed and neoformed tissue was found at the level of the sx cavernous sinus. On day 50, the appearance of sx eye pain was observed and, upon encephalo-CT, bone rarefaction of the sx sphenoidal sinus was found. On day 60, a transphenoidal biopsy of the mucosa of the sx sphenoidal sinus and of the neoformed tissue of the cavernous sinus was performed. On day 69, histological examination of the transcranial biopsy showed inflammatory tissue with non-septate fungal hyphae. The patient was subjected to antifungal treatment with L-amB at a dosage of 5 mg/kg/die. On day 75, culture and molecular examination, also performed by micromanipulation on an individual fungal cell, characterized Invasive Mucormycosis by *Rizhopus* spp. Posaconazole at a dosage of 800 mg/die was combined with the treatment in progress. On day 82, the patient, who had achieved complete remission of the haemopathy, was discharged with purely oral treatment with posaconazole. Currently, the patient is still in LAP molecular remission after having completed 4 maintenance cycles with arsenic trioxide and ATRA. The treatment with posaconazole is currently still in progress. Upon a latest, recent check with NMR the inflammatory/infective tissue of the sx sphenoidal sinus had reduced in size and the symptomology, including the diplopia, was on the way to complete resolution.

In patient 1, the ELISPOT method according to the present invention was performed at the time at which chemotherapy started (day 1), between the second and third HRCTs (day 27), 2 days before the third HRCT of the thorax (day 34) and subsequently on days 51 and 64 and on day 238. The ELISPOT was negative for the presence of Mucorales-specific T cells in the first and last determinations, in the absence and upon resolution of the infective pathology, whereas it was positive in the determinations that were performed in concomitance with the pulmonary infection by Mucorales. In particular, the ELISPOT method according to the present invention showed: 1) the presence of Mucorales-specific T cells, polarized towards a Th2-type immunity and producing IL-10 on days +27 and +64; 2) the presence of Mucorales-specific T cells polarized towards a Th1-type immunity and producing IFN-γ in the determinations of days +27, +34 and +51; 3) a decreasing ratio between the number of IL-10 producing cells and that of IFN-γ producing cells in the determinations of days +27, +34 and +51 (FIG. 1A). In patient 2, the ELISPOT method according to the present invention was performed on peripheral blood samples collected on days 36, 55, 68, 75 and 82 from the start of the immunosuppressive therapy, respectively. The ELISPOT was positive for the presence of solely Interleukin-10 producing Mucorales-specific T cells upon the first determination (36) and positive for the presence of both IL-4 and IL-10 producing Mucorales-specific T cells, and hence indicative of a Th2-type response, in the subsequent determinations (55, 68, 75, 82). In the three determinations (55, 68, 72), the ELISPOT was positive for the presence of Mucorales-specific interferon-gamma (IFN-γ) producing T cells which are indicative of a Th1-type response (FIG. 1B).

In patient 3, the ELISPOT method was performed on day 75 and on day 95 of the induction therapy, on day 48 (day 137 from the start of the treatment), on day 55 (day 143 from the start of treatment) of the maintenance therapy, and on day 217 from the start of the treatment. The ELISPOT was positive solely for a Mucorales-specific, IL-10 producing T cell response in the first and second determinations and for a Mucorales-specific IFN-γ producing and hence Th1 and IL-4 producing T cell response in the third and fourth determinations. The ELISPOT was negative for Mucorales-specific T cells in the last determination in concomitance with the almost complete resolution of the infective episode (FIG. 1C).

CLINICAL RESULTS

The method according to the present invention thus provided proof of Mucormycosis in all three patients. In particular, the positivity of the ELISPOT according to the present invention was the sole proof of the infection in patient 1, as early as day 27. In this patient, the diagnosis was reached, one month afterwards, solely by surgical intervention, only on day 42, all of the other methods having been negative. In patient 2 and in patient 3, ELISPOT provided a valid support for histological and cultural diagnosis, representing the sole non-cultural and non-invasive positive result.

FIG. 2 shows the results of ELISPOTs in patients affected by pulmonitis with non-fungal aetiology, used as negative controls.

The invention claimed is:

1. A method of diagnosing and/or monitoring invasive Mucormycosis in a patient having said Mucormycosis due to a fungal pathogen of the order Mucorales, the method comprising performing an in vitro assay, wherein a biological fluid obtained from the patient is contacted with an antigen extractable from conidia and/or hyphae of the fungal pathogen of the order Mucorales and determining the number of specific IFN-producing T cells, specific IL-10-producing T cells, and specific IL-4-producing T cells, wherein the T cells are specific to the antigen.

2. The method of claim 1, wherein the in vitro assay is an immunoenzymatic assay.

3. The method of claim 2, wherein the immunoenzymatic assay is an ELISPOT assay.

4. The method of claim 2, wherein the immunoenzymatic assay is a Quantiferon assay.

5. The method of claim 1, wherein the assay is an immunocytofluorometric assay.

6. The method of claim 5, wherein the immunocytofluorometric assay is cytokine secretion assay (CSA) or intracellular cytokine staining (ICS) assay.

7. The method of claim 1, wherein the biological fluid is blood, bronchioalveolar lavage liquid and/or pleural fluid.

8. The method of claim 1, wherein the antigen is a proteinaceous extract.

9. The method of claim 1, wherein the positivity threshold number for the specific IFN-producing T cells, specific IL-10-producing T cells, and specific IL-4-producing T cells is between 2 to 10 spot forming cells (SFCs).

10. The method of claim 1, wherein the method comprises the following steps:
    (a) culture of the fungal pathogen of the order Mucorales in Saboraud's culture medium for 2-4 days;
    (b) subsequent collection of the conidia by washing of the surface layer of the fungal culture with sterile water;
    (c) subsequent filtration and centrifugation of the washed conidia to obtain the conidia pellet;
    (d) subsequent suspension of the conidia pellet in liquid Saboraud culture medium and stirring for about 12 hours to achieve germination of the conidia;
    (e) subsequent washing of the germinated conidia in a saline solution;
    (f) subsequent deactivation of the germinated conidia by heat at 100° C. for 1 hour;
    (g) subsequent sonication of the heat-deactivated germinated conidia and
    (h) subsequent resuspension of the sonicated conidia from step (g) in a saline solution or in a fungal culture medium; and
    (i) subsequent optional freezing.

11. The method of claim 1, wherein the method comprises the following steps:
    (j) culture of the fungal pathogen of the order Mucorales in Saboraud's agar culture plates;
    (k) subsequent collection of the hyphae followed by suspension of the hyphae in sterile water;
    (l) subsequent filtration and centrifugation of the hyphae suspended in sterile water to obtain the hyphae mycete pellet;
    (m) subsequent freezing and thawing of the mycete pellet;
    (n) subsequent homogenization of the mycete pellet in the presence of equal volume of beads made of inert material or glass equal to the volume of the mycete and
    (o) subsequent centrifugation with subsequent optional freezing.

* * * * *